United States Patent

Kaschig et al.

Patent Number: 5,942,564
Date of Patent: *Aug. 24, 1999

[54] HYDROXYPHENYL-S-TRIAZINES

[75] Inventors: Jürgen Kaschig, Freiburg; Dieter Reinehr, Kandern, both of Germany; Manfred Rembold, Pfeffingen, Switzerland

[73] Assignee: Ciba Specialty Chemicals Corporation, Tarrytown, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/783,184

[22] Filed: Jan. 15, 1997

Related U.S. Application Data

[62] Division of application No. 08/392,782, filed as application No. PCT/EP93/02316, Aug. 27, 1993.

[30] Foreign Application Priority Data

Sep. 7, 1992 [CH] Switzerland .............. 2801/92

[51] Int. Cl.$^6$ ...................................... C08K 5/34
[52] U.S. Cl. .............................. 524/100; 524/91
[58] Field of Search ........................ 524/91, 100

[56] References Cited

U.S. PATENT DOCUMENTS

| | | | |
|---|---|---|---|
| 4,619,956 | 10/1986 | Susi | 524/87 |
| 5,300,414 | 4/1994 | Leppard et al. | 430/507 |
| 5,410,048 | 4/1995 | Leppard et al. | 544/216 |

FOREIGN PATENT DOCUMENTS

| | | |
|---|---|---|
| 0434608 | 6/1991 | European Pat. Off. . |
| 0444323 | 9/1991 | European Pat. Off. . |
| 975966 | 11/1964 | United Kingdom . |

Primary Examiner—Kriellion S. Morgan
Attorney, Agent, or Firm—Luther A. R. Hall

[57] ABSTRACT

The invention relates to o-hydroxyphenyl-s-triazines of formula

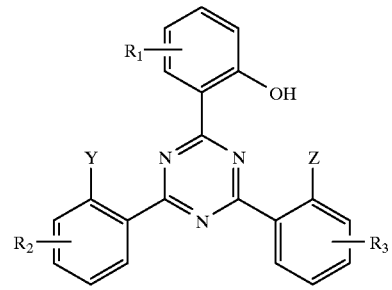

(1)

wherein at least one of Y and Z are $C_1$–$C_{18}$ alkoxy

The compounds are suitable for use as UV stabilisers for the photochemical and thermal stabilisation of polyester fibre materials and as stabilisers for organic ploymers.

6 Claims, No Drawings

HYDROXYPHENYL-S-TRIAZINES

This application is a divisional of application Ser. No. 08/392,782, filed on Feb. 28, 1995, now abandoned filed as application Ser. No. PCT/EP93/02316 filed on Aug. 27, 1993.

The present invention relates to o-hydroxyphenyl-s-triazines, to a process for the preparation of these compounds, to a process for simultaneously dyeing or printing and photochemically and thermally stabilising polyester fibre materials, to the use of said compounds as stabilisers for organic polymers, and to the polymer stabilised with said compounds.

Hydroxyphenyl-s-triazines that carry at least two o-hydroxyphenyl substituents are known, inter alia, from Helv. Chim. Act. 55(1), 1566–1595 (1972). The shortcoming of these compounds, is however, that their maximum absorption spectra are of relatively long wavelength and they therefore normally have an undesirable inherent colour.

Surprisingly, it has now been found that certain s-triazines that have only one o-hydroxy function have a maximum absorption spectrum of substantially shorter wavelength. Such compounds are better able to absorb in particular energy-rich radiation and, because of their insignificant inherent colour, are suitable for use as UV stabilisers in synthetic materials and resins, especially polyesters.

Accordingly, the present invention relates to o-hydroxyphenyl-s-triazines of formula

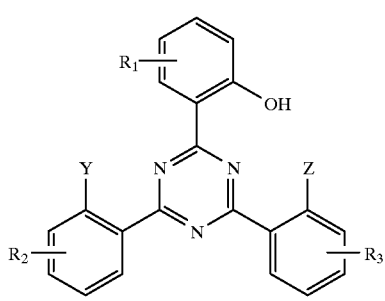

(1)

wherein $R_1$, $R_2$ and $R_3$ are each independently of one another hydrogen, halogen, $C_1$–$C_{18}$alkyl or $C_1$–$C_{18}$alkoxy, and Y and Z are each independently of the other hydrogen or $C_1$–$C_{18}$alkoxy, with the proviso that one of the substituents Y and Z is always $C_1$–$C_{18}$alkoxy, and, if $R_2$ and $R_3$, Y and Z are each $C_1$–$C_{18}$alkoxy, $R_1$ is not hydrogen.

$C_1$–$C_{18}$Alkyl and $C_1$–$C_{18}$alkoxy are straight-chain or branched alkyl or alkoxy, typically including methyl, ethyl, n-propyl, isopropyl, n-butyl, sec-butyl, tert-butyl, amyl, isoamyl or tert-amyl, heptyl, octyl, isooctyl, nonyl, undecyl, dodecyl, tetradecyl, pantadecyl, hexadecyl, heptadecyl or octadecyl, and, respectively, methoxy, ethoxy, propoxy, butoxy, pentyloxy, hexyloxy, heptyloxy, octyloxy, isooctyloxy, nonyloxy, undecyloxy, dodecyloxy, tetradecyloxy, pentadecyloxy, hexadecyloxy, heptadecyloxy or octadecyloxy.

Halogen is chloro, bromo or iodo. Chloro is preferred.

Suitable compounds of formula (1) are preferably those in which Y and Z are $C_1$–$C_{12}$alkoxy, and $R_1$, $R_2$ and $R_3$ have the meanings assigned to them.

Particularly preferred compounds of formula (1) are those wherein Y and Z are $C_1$–$C_{12}$alkoxy, and $R_1$, $R_2$ and $R_3$ are each hydrogen.

Particularly preferred triazines are those wherein Y and Z are $C_1$–$C_4$alkoxy.

Further interesting compounds of formula (1) are those wherein

Y is $C_1$–$C_{12}$alkoxy, $R_1$ and $R_3$ are hydrogen or $C_1$–$C_{12}$alkoxy, and $R_2$ and Z are each hydrogen, and, in particular, those compounds wherein $R_1$ and $R_3$ are $C_1$–$C_{12}$alkoxy, and, most preferably, those compounds wherein $R_1$ and $R_3$ are $C_1$–$C_4$alkoxy.

Particularly important compounds have the formula

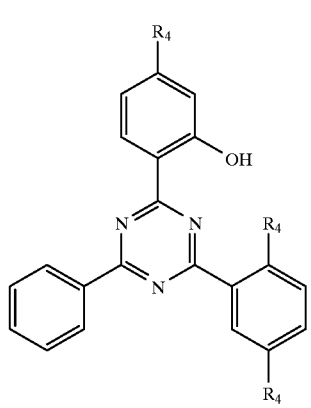

(2)

wherein the $R_4$ substituents are each independently of one another $C_1$–$C_4$alkoxy.

Illustrative examples of compounds of formula (1) are:

2-(2'-methoxyphenyl)-4-(2'-hydroxyphenyl)-6-phenyl-s-triazine 2-(4'-methoxyphenyl)-4-(2'-hydroxyphenyl)-6-phenyl-s-triazine 2-(2'-methoxy4'-methylphenyl)-4-(2'-hydroxy)-4'-methylphenyl)-6-phenyl-s-triazine 2-(2'-methoxy-5'-methylphenyl)-4-(2'-hydroxy-5'-methylphenyl)-6-phenyl-s-triazine 2-(2'-hydroxy-4'-methoxyphenyl))-4-(2',4'-dimethoxyphenyl)-6-phenyl-s-triazine 2-(2',4'-diisopropoxyphenyl)-4-(2'-hydroxy-4'-isopropoxyphenyl)-6-phenyl-s-triazine 2-(2',4'-dioctyloxyphenyl)-4-(2'-hydroxy-4'-octyloxyphenyl)-6-phenyl-s-triazine 2,4-bis(2'-methoxyphenyl)-6-(2'-hydroxyphenyl)-s-triazine 2,4-bis(2'-methoxy-4'-methylphenyl)-6-(2'-hydroxy-4'-methylphenyl)-s-triazine 2,4-bis(2'-methoxy-5'-methylphenyl)-6-(2'-hydroxy-5'-methylphenyl)-s-triazine 2,4-bis(2',4'-dimethoxyphenyl)-6-(2'-hydroxy-4'-methoxyphenyl)-s-triazine.

The compounds of formulae (1) and (2) may conveniently be prepared by selective alkylation of the hydroxy groups of corresponding triazines. The starting compounds must contain at least two hydroxyl groups. This process is novel and constitutes a further object of the invention. The process for the preparation of the triazines of formula (1) comprises selectively alkylating a hydroxyphenyl-s-triazine of formula

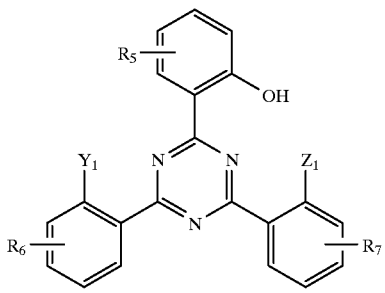

(3)

wherein $R_5$, $R_6$, $R_7$ are each independently of one another hydrogen, halogen, $C_1$–$C_{18}$alkyl or $C_1$–$C_{18}$alkoxy, and $Y_1$ and $Z_1$ are each independently of the other hydrogen or hydroxy, with the proviso that at least one of $Y_1$ and $Z_1$ is hydroxy, with an alkylating reagent.

Suitable alkylating reagents are alkyl halides, dialkyl sulfates, toluenesulfonates or dialkylalkane phosphonates. It is preferred to use dialkylalkane phosphonates. Dimethyl sulfate is used for the methylation on account of its reactivity and low cost.

The alkylation reaction is carried out using sodium or potassium carbonate or dilute sodium or potassium hydroxide solution. In practice, the procedure typically comprises mixing the starting compound, alkali metal carbonate or sodium hydroxide solution together with the alkylating reagent, and stirring the mixture in the temperature range from 20 to 170° C. for 1 to 7 hours. A further solvent for the reaction is not necessary. The process is carried out under anhydrous conditions when using dialkylalkane phosphonate as alkylating reagent. After conventional working up, the product of formula (1) is obtained in good yield and high purity.

The starting compounds of formula (3) are known, inter alia from Helv. Chim. Act 55(1), 1566–1595 (1972), or from the references cited therein.

The compounds of formula (1) are suitable for use as stabilisers, i.e. for protecting UV-sensitive organic materials, especially textile fibre materials, from the harmful action of ultraviolet radiation.

The invention therefore further relates to a process for dyeing or printing and photochemically and thermally stabilising polyester fibre materials, which comprises treating said fibre material by adding to the aqueous dye liquor or print paste a compound of formula

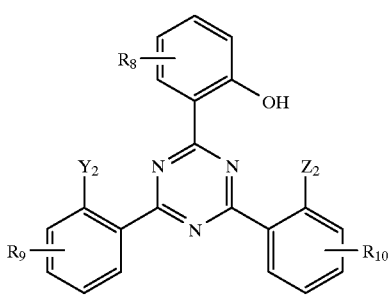

(4)

wherein $R_8$, $R_9$ and $R_{10}$ are each independently of one another hydrogen, halogen, $C_1$–$C_{18}$alkyl, $C_1$–$C_{18}$alkoxy, carboxyalkoxy of not more than 8 carbon atoms, and $Y_2$ and $Z_2$ are each independently of the other hydrogen or $C_1$–$C_{18}$alkoxy.

The compounds of formula (1) are also admirably suitable for the process.

It is preferred to use for the process compounds of formula (4), wherein $R_8$, $R_9$ and $R_{10}$ are each independently of one another hydrogen, halogen, $C_1$–$C_{12}$alkyl or $C_1$–$C_{12}$alkoxy, and $Y_2$ and $Z_3$ are each independently of the other hydrogen or $C_1$–$C_{12}$alkoxy.

The triazines of formula (4) of this invention are used in an amount of 0.01 to 10% by weight, preferably 0.1 to 5% by weight, based on the weight of the fibre material.

The triazines of formula (4) are sparingly soluble in water and are therefore applied in dispersed form. To this end they are milled with an appropriate dispersant in a quartz bead mill or with an impeller to a particle size of c. 1–2 μm.

Suitable dispersants for the UV absorbers of formula (4) are:

acid esters or their salts of alkylene oxide adducts, typically acid esters or their salts of a polyadduct of 4 to 40 mol of ethylene oxide with 1 mol of a phenol, or phosphated polyadducts of 6 to 30 mol of ethylene oxide with 1 mol of 4-nonylphenol, 1 mol of dinonylphenol or, preferably, with 1 mol of compounds which are prepared by addition of 1 to 3 mol of optionally substituted styrenes to 1 mol of phenol, polystyrene sulfonates, fatty acid taurides, alkylated diphenyl oxide mono- or disulfonates, sulfonates of polycarboxylates, the polyadducts of 1 to 60 mol, preferably 2 to 30 mol of ethylene oxide and/or propylene oxide with fatty amines, fatty amides, fatty acids or fatty alcohols, each containing 8 to 22 carbon atoms in the alkyl chain, with trihydric to hexahydric alkanols containing 3 to 6 carbon atoms, which polyadducts are converted into an acid ester with an organic dicarboxylic acid or with an inorganic polybasic acid, ligninsulfonates, and, most preferably, formaldehyde condensates such as condensates of ligninsulfonates and/or phenol and formaldehyde, condensates of formaldehyde with aromatic sulfonic acids, typically condensates of ditolyl ether sulfonates and formaldehyde, condensates of naphthalenesulfonic acid and/or naphthol- or naphthylaminesulfonic acids with formaldehyde, condensates of phenolsulfonic acids and/or sulfonated dihydroxydiphenylsulfone and phenols or cresols with formaldehyde and/or urea, as well as condensates of diphenyl oxide-disulfonic acid derivatives with formaldehyde.

Suitable dyes are disperse dyes which are only sparingly soluble in water. They are therefore present in the dye liquor mostly in the form of a fine dispersion. They may belong to different dye classes, including the acridone, azo, anthraquinone, coumarin, methine, perinone, naphthoquinone-imine, quinophthalone, styryl or nitro dyes. Mixtures of disperse dyes may also be used in the practice of this invention.

Polyester fibre material which can be dyed or printed and treated with the cited UV absorbers will be understood as including cellulose ester fibres such as cellulose secondary acetate and cellulose triacetate fibres and, preferably, linear polyester fibres which may also be acid-modified, and which are obtained by the condensation of terephthalic acid with ethylene glycol or of isophthalic acid or terephthalic acid with 1,4-bis(hydroxymethyl)cyclohexane, as well as copolymers of terephthalic and isophthalic acid and ethylene glycol. The linear polyester fibre material hitherto used almost exclusively in the textile industry consists of terephthalic acid and ethylene glycol.

The fibre materials may also be used as blends with each other or with other fibres, typically blends of polyacrylonitrile/polyester, polyamide/polyester, polyester/cotton, polyester/viscose and polyester/wool, and they can be dyed or also printed batchwise or continuously.

The textile material can be in different forms of presentation, preferably as piece goods such as knitgoods or wovens or also as yarn on cheeses, warp beams and the like.

Textile fabrics in the outerwear garment sector which are transparent are also very suitable for the process of this invention. Textiles treated by the inventive process are able to protect the skin tissue beneath the transparent outerwear garment fabric from the harmful effects of UV radiation.

Dyeing is carried out from an aqueous liquor by a continuous or batch process. In batchwise dyeing, the liquor ratio may be chosen over a wide range, typically from 1:4 to 1:100, preferably from 1:6 to 1:50. The dyeing temperature is at least 50° C. and is normally not higher than 140° C. The preferred temperature range is from 80 to 135° C.

In continuous dyeing methods, the dye liquors, which may contain further auxiliaries in addition to the dyes, are applied to the piecegoods by padding or slop-padding and developed by thermofixation or HT steaming processes.

Linear polyester fibres and cellulose fibres are preferably dyed by the high temperature process in closed and pressure-resistant apparatus in the temperature range >100° C., preferably in the range from 110 to 135° C., and under normal or elevated pressure. Suitable closed apparatus includes typically circulation dyeing machines such as cheese or beam dyeing machines, winch becks, jet or drum dyeing machines, muff dyeing machines, paddles or jiggers.

Cellulose secondary acetate is preferably dyed in the temperature range from 80–85° C.

The procedure for using the UV absorbers of the present invention for dye application is such that the fibre material is treated simultaneously in the dyebath with the UV absorber and the dye.

The dye liquors may also contain further ingredients such as dyeing assistants, dispersants, carriers, wool protectives, and wetting agents as well as antifoams.

The dyebaths may also contain mineral acids, typically sulfuric acid or phosphoric acid, or conveniently organic acids, typically aliphatic carboxylic acids such as formic acid, acetic acid, oxalic acid or citric acid and/or salts such as ammonium acetate, ammonium sulfate or sodium acetate. The acids are used in particular to adjust the pH of the liquors used in the practice of this invention to 4–5.

Preferably the fibre material is first run for 5 minutes at 40–80° C. in the bath which contains the dye, the UV absorber and any further auxiliaries and which has been adjusted to pH 4.5–5.5, then the temperature is raised to 125–130° C. over 10 to 20 minutes, and further treatment is carried out for 15 to 90 minutes, preferably for 30 minutes, at this temperature.

The dyeings are finished by cooling the dye liquor to 50–80° C., rinsing the dyeings with water and, if necessary, reduction clearing them in conventional manner in alkaline medium. The dyeings are then again rinsed and dried. When using vat dyes for dyeing the cellulose component, the goods are first treated with hydrosulfite at pH 6–12.5, then treated with an oxidising agent and finally washed off.

For producing prints, the triazines of the present invention are mixed in the form of aqueous dispersions with the print pastes. The print paste then contains the appropriate triazine in an amount of 0.1 to 10%, preferably 0.1 to 5%, based on the weight of the print paste.

The amount of the dyes added to the print pastes will depend on the desired shade. Amounts of 0.01 to 15% by weight, preferably of 0.02 to 10% by weight, have generally been found useful.

In addition to the dyes and the aqueous dispersion of the UV absorber, the print pastes conveniently contain acid-stable thickeners, preferably of natural origin such as carob bean flour derivatives, especially sodium alginate by itself or in admixture with modified cellulose, preferably with 20 to 25% by weight of carboxymethyl cellulose. In addition, the print pastes may further contain acid donors such as butyrolactone or sodium hydrogen phosphate, preservatives, sequestering agents, emulsifiers, water-insoluble solvents, oxidising agents or deaerators.

Particularly suitable preservatives are formaldehyde donors such as paraformaldehyde or trioxane, preferably c. 30 to 40% by weight aqueous formaldehyde solutions. Suitable sequestering agents are sodium nitrilotriacetate, sodium ethylenediaminetetraacetate preferably sodium polymethaphosphate, more particularly sodium hexamethaphosphate. Emulsifiers are preferably polyadducts of an alkylene oxide and a fatty alcohol, more particularly a polyadduct of oleyl alcohol and ethylene oxide. Water-insoluble solvents are preferably high-boiling saturated hydrocarbons, more particularly paraffins having a boiling range from about 160 to 210° C. (white spirits). Oxidising agents are typically aromatic nitro compounds, preferably an aromatic mono- or dinitrocarboxylic acid or mono- or dinitrosulfonic acid which may be in the form of an alkylene oxide polyadduct, preferably a nitrobenzenesulfonic acid. Deaerators are suitably high-boiling solvents, preferably terpentine oils, higher alcohols, $C_8$–$C_{10}$alcohols, terpene alcohols or deaerating agents based on mineral and/or silicone oils, preferably commercial formulations comprising about 15–25% by weight of a mixture of mineral and silicone oils and about 75–85% by weight of a $C_8$alcohol such as 2-ethyl-n-hexanol.

For printing the fibre materials, the print paste is applied direct to the whole or to a part of the surface, conveniently using printing machines of conventional construction, typically rotogravure, rotary screen printing and flat screen printing machines.

The fibre material is dried after printing in the temperature range up to 150° C., preferably in the range from 80 to 120° C.

The subsequent fixation of the fibre material is carried out by a heat treatment, preferably in the temperature range from 100 to 220°. The heat treatment is normally carried out with superheated steam under atmospheric pressure.

Depending on the temperature, fixation is carried out for 20 seconds to 10 minutes, preferably for 4 to 8 minutes.

The prints are also finished in conventional manner by rinsing with water, followed by an optional reductive afterclear in alkaline medium, conveniently with sodium dithionite. In this last mentioned case, the prints are again rinsed, hydroextracted and dried.

The process of this invention makes it possible to obtain dyeings and prints of superior lightfastness and sublimation fastness on polyester material. A specific pre- or aftertreatment of the fibre material is not necessary in the inventive process.

The compounds of formula (4) may be used with advantage as stabilisers for protecting organic polymers against degradation induced by light, oxygen and heat. The invention therefore also relates to a process for stabilising organic polymers against degradation induced by light, oxygen and heat, which comprises blending said materials with at least one compound of formula (4). Illustrative examples of such polymers to be stabilised are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
   a) radical polymerisation (normally under high pressure and at elevated temperature).
   b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon mon-oxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

The use of the novel compounds as stabilisers in surface-coating compositions of all kinds is especially preferred. The invention thus relates to a method as described above, wherein the organic polymer is a binder for a surface-coating composition. Surface-coating compositions may be, for example, pigmented or unpigmented paint or varnish compositions or metallic paints. They may contain an organic solvent or be solventless, or they may be water-based paints.

The surface-coating compositions may contain as binder a polymer selected from those cited previously. Illustrative examples of surface-coating compositions containing special binders are the following:

1. surface-coating compositions based on cold- or hot-crosslinkable alkyd, acrylate, polyester, epoxy or melamine resins or mixtures of said resins, to which an optional acid curing catalyst is added;

2. two-component polyurethane surface-coating compositions based on hydroxylated acrylate, polyester or polyether resins and aliphatic or aromatic polyisocyanates;

3. single component polyurethane surface-coating compositions based on blocked polyisocyanates which are deblocked during stoving;

4. two-component surface-coating compositions based on (poly)ketimines and aliphatic or aromatic polyisocyanates;

5. two-component surface-coating compositions based on (poly)ketimines and an unsaturated acrylate resin or a polyacetoacetate resin or a methyl acrylamidoglycolate methyl ester;

6. two-component surface-coating compositions based on carboxyl or amino group containing polyacrylates and polyepoxides;

7. two-component surface-coating compositions based on anhydride group containing acrylate resins ad a polyhydroxy or polyamino component;

8. two-component surface-coating compositions based on (poly)oxazolidines and anhydride group containing acrylate resins or unsaturated acrylate resins or aliphatic or aromatic polyisocyanates;

9. two-component surface-coating compositions based on unsaturated polyacrylates and polymalonates;

10. thermoplastic polyacrylate surface-coating compositions based on thermoplastic acrylate resins or not self-crosslinking acrylate resins in conjunction with etherified melamine resins;

11. surface-coating systems based on siloxane-modified or fluorine-modified acrylate resins.

The surface-coating compositions may also be photocurable compositions, in which case the binder consists of monomer or oligomer compounds which contain ethylenic double bonds and which are converted by actinic light or with electron beams into a crosslinked high molecular weight form. The binder is usually a mixture of such compounds.

The surface-coating compositions may be applied as single layer or two-layer systems, in which case the stabilisers of this invention are preferably added to the unpigmented topmost layer.

The surface-coating compositions can be applied to the substrates (metal, plastic, wood and the like) by the conventional techniques, for example by brushing, spraying, coating, immersion or electrophoresis.

The amount of stabiliser of formula (4) added will depend on the respective substrate and the intended end use. Normally amounts from 0.01 to 5% by weight will suffice. It is preferred to use from 0.05 to 3% by weight, based on the polymer to be stabilised. In the practice of this invention, polymers containing 0.01 to 5% by weight, more particularly 0.05 to 3% by weight, of at least one compound of formula (4) are preferred.

In certain cases it may be useful to use two or more compounds of formula (4). Furthermore, one or more other stabilisers and/or other additives may be used concurrently, as typically the following types of compounds:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-methyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures therof 1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of $\beta$-(3,5-di-tert-butyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3,5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexoxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexoxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1 '-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl 4-piperidyl)pyrrolidin-2,5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxydisubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy4-octyloxyphenyl)4,6-bis(2,4-dimethylphenyl)-1,3,5-triazine, 2-(2,4-dihydroxyphenyl)4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetaladipoyl dihydrazide, N,N'-bis(salicyloyl) oxalyl dihydrazide, N,N'-bis(salicyloyl)thiopropionyl dihydrazide.

4. Further phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxy-pentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863 or U.S. Pat. No. 4,338,244.

Particularly important stabilised polymers are those having an additional content of a light stabiliser selected from the class of the sterically hindered amines and/or the class of the 2-(2'-hydroxyphenyl)benzotriazoles. By sterically hindered amines are meant in particular those compounds which contain in the molecule one or more groups of formula

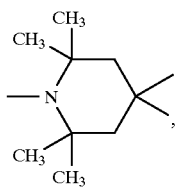

, which compounds may be monomeric, oligomeric or polymeric.

Examples of such compounds will be found in item 2.6 of the list of possible additional stabilisers.

The incorporation of the compounds of formula Ia or Ib and further optional additives in the polymers can be made before or during the processing of the polymers to shaped articles, conveniently by blending them in powder form or by addition to the melt or solution of the polymer or to a suitable surface-coating composition which contains a polymeric binder.

The invention therefore also relates to the polymers stabilised by addition of at least one compound of formula (4), which polymers may contain other optional modifiers. The stabilised polymers can be used in different forms, as for example filaments, sheets, ribbons, profiles, hollow bodies, boards, double-walled boards, or as binders for paints and varnishes, adhesives and putty. Their use in surface-coating compositions is of particular interest.

In the following Examples percentages are by weight. The amounts of dye and triazines are based on pure substance.

Preparation of the novel compounds

EXAMPLE 1

2-(2'-methoxyphenyl)-4-(2'-hydroxyphenyl)-6-phenyl-s-triazine 9.6 g (0.028 mol) of 2,4-bis(2'-hydroxyphenyl)-6-phenyl-s-triazine, 25 ml (0.234 mol) of dimethylmethane phosphonate and 4.0 g (0.028 mol) of sodium carbonate are mixed and the mixture is heated to 150° C. After 2 hours the clear, pale red reaction solution is stirred into 150 ml of ethanol. The precipitate is filtered with suction, rinsed with 20 ml of ethanol and water and dried in an exsiccator, giving 9.4 g (94.1%) of the compound of formula

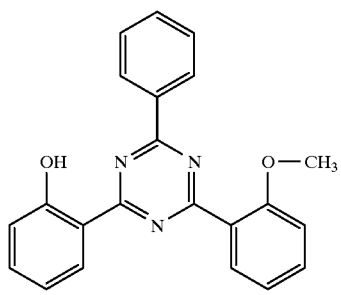

(101)

Melting point: 153–155° C.
UV spectrum ($5–10^{-5}$ mol/l in chloroform):
$\lambda_{max}/\epsilon_{max}$=275/49580 331/14260

EXAMPLE 2

2,4-bis(2'-methoxyphenyl)-6-(2'-hydroxyphenyl)-s-triazine Alkylation with dimethyl sulfate 53.6 g 2,4,6-tris(2'-hydroxyphenyl)-s-triazine prepared according to GB-A-1 294 322) are charged to 500 ml of a mixture of acetone/$H_2O$ (ratio 8:2). After the dropwise addition of 25.2 g of a 50% solution of sodium hydroxide, 41.6 g of dimethyl sulfate are added to the solution over 45 minutes and the reaction mixture is stirred for about 5 hours at 45–59° C. The reaction mixture is poured into 1 liter of water, extracted with 300 ml of toluene and the toluene phase is concentrated to dryness, giving 58.9 g of the compound of formula

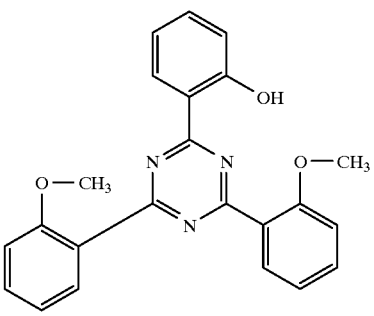

(102)

as a yellowish powder.
m.p.: 113–114° C.

EXAMPLE 3

2,4-bis(2'-methoxyphenyl)-6-(2'-hydroxyphenyl)-s-triazine Alkylation with dimethylmethane phosphonate 17.9 g of 2,4,6-tris(2'-hydroxyphenyl)-s-triazine and 10.9 g of sodium carbonate are suspended in 150 ml of dimethylmethane phosphonate (DMMP) and the suspension is stirred for 7 hours at 140–160° C. After working up, the compound of formula (102) is obtained.

The compounds (103)–(111) in Table 1 are prepared in analogous manner.

TABLE 1

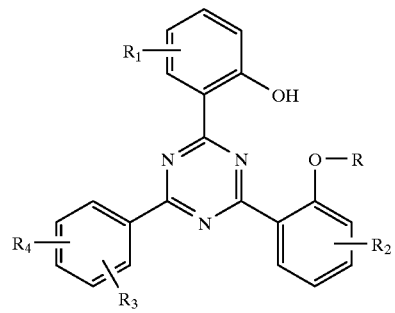

| Cmpd No. | R | $R_1$ | $R_2$ | $R_3$ | $R_4$ | $\lambda_{max}$* | $\epsilon$* | Fp.[°C.] |
|---|---|---|---|---|---|---|---|---|
| (103) | $CH_3$ | 4-$OCH_3$ | 4-$OCH_3$ | 2-$OCH_3$ | 4-$OCH_3$ | 332 | 50750 | 192–193 |
| (104) | $CH_3$ | 4-$CH_3$ | 4-$CH_3$ | H | H | 391 | 19500 | 220–221 |
| (105) | $CH_3$ | 4-$OCH_3$ | 4-$OCH_3$ | H | H | 334 | 36400 | 167–168 |
| (106) | $CH_3$ | 4-$CH_3$ | 4-$CH_3$ | 2-$OCH_3$ | 4-$CH_3$ | 344 | 31150 | 255–256 |
| (107) | $CH_3$ | 5-$CH_3$ | 5-$CH_3$ | 2-$OCH_3$ | 5-$CH_3$ | 356 | 20850 | 170–171 |
| (108) | $CH_3$ | 5-$CH_3$ | 5-$CH_3$ | H | H | 344 | 12950 | 240–242 |
| (109) | $CH(CH_3)_2$ | 4-$O(CH)(CH_3)_2$ | 4-$O(CH)(CH_3)_2$ | H | H | 338 | 34600 | 150–151 |
| (110) | $(CH_2)_7CH_3$ | 4-$O(CH_2)_7CH_3$ | 4-$O(CH_2)_7CH_3$ | H | H | 339 | 42400 | 75–77 |
| (111) | $CH_3$ | 4-$OCH_3$ | 4-O—$CH_3$ | 4-Cl | H | | | |

*UV spectrum ($5 \cdot 10^{-5}$ mol/l in chloroform)

Application Examples

EXAMPLE 4

Eleven 10 g samples of PES tricot are dyed in a HT dyeing machine, e.g. ®Labomat (supplied by Mathis, Niederhasli) at a liquor ratio of 1:10. The liquors contain 2 g/l of ammonium sulfate, 0.5 g/l of a dyeing auxiliary such as ®Univadin 3-flex and the dyes in the following amounts:

0.210% of dye (1) C.I. DISPERSE YELLOW 42
0.087% of dye (2) C.I. DISPERSE RED 30
0.080% of dye (3) C.I. DISPERSE VIOLET 57
0.087% of dye (4) C.I. DISPERSE BLUE 60.

Whereas liquor (I) contains no further ingredients (stabilisers), 0.6% of each of the numbered compounds in Table 2 is added to liquors (II)–(XI).

The compounds were milled beforehand with 2 parts of a nonionic dispersant in a ball mill or with an impeller to a particle size of 1–2 μm.

The tricot samples are dyed in the dispersed liquors in pressure bombs. The samples are put into the liquors at 50° C. and after a treatment time of 5 minutes heated to 130° C. at a rate of 3° C./min. Dyeing is carried out for 45 minutes at this temperature and then, after cooling to 50° C., the dyed samples are rinsed thoroughly with demineralised water and dried.

The lightfastness properties are determined by irradiating the dyeings in accordance with DIN 75.202 (FAKRA) and SAE J 1885. The results are reported in Table 2.

|  | Liquor | Colour distance factor ΔE (DIN 6174) | |
|---|---|---|---|
|  |  | 260 h FAKRA | 488 kJ SAE J 1085 |
| (I) | none* | 4.4 | 6.7 |
| (II) | 0.6% (112) | 2.2 | 2.9 |
| (III) | 0.6% (101) | 2.4 | 3.7 |
| (IV) | 0.6% (104) | 3.7 | 5.9 |
| (V) | 0.6% (102) | 1.2 | 2.3 |
| (VI) | 0.6% (105) | 1.9 | 3.0 |
| (VII) | 0.6% (106) | 3.5 | 5.9 |
| (VIII) | 0.6% (103) | 3.3 | 4.1 |
| (IX) | 0.6% (107) | 1.8 | 3.9 |
| (X) | 0.6% (108) | 3.7 | 5.5 |
| (XI) | 0.6% (109) | 2.9 | 4.2 |

*Average of 10 measurements

The compound (112) has the following structure:

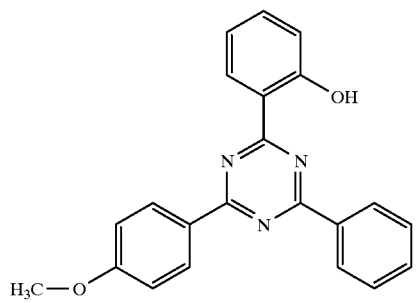

(112)

UV spectrum ($5-10^{-5}$ mol/l in chloroform):
$\lambda_{max}$=278 and 311
$\epsilon_{max}$=37660 and 29700

The results in Table 2 show that the lightfastness properties of the fibre materials treated by the inventive process are markedly better than those of untreated material.

EXAMPLE 5

With stirring, 10 g of polycarbonate powder (Lexan® 115) are dissolved at room temperature in 50 g of methylene chloride. The time taken is several hours. To the solution is added 0.2 g of UV absorber, corresponding to a concentration of 2%. Films of 20 μm thickness are cast from these solutions.

The films are irradiated in an Atlas Weatherometer CI 65 at a black standard temperature of 63° C., a relative humidity of 60% and at an intensity of 0.35 W/m² (340 nm) until embrittlement, which is indicated by the formation of cracks in the films. The exposure time until embrittlement is given in Table 1.

TABLE 1

| Exposure time (h) until embrittlement | |
|---|---|
| UV Absorber of formula | Exposure time (h) until embrittlement |
| without UV absorber | 1375 |
| (101) | 3840 |
| (102) | 3180 |
| (103) | 2850 |
| (105) | 3510 |
| (106) | >4677 |
| (113) | 3350 |

The compound of formula (113) has the following structure:

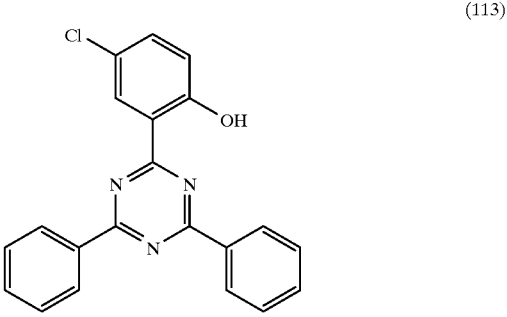

(113)

EXAMPLE 6

The novel light stabilisers are tested in a 2 layer metallic paint. The light stabilisers are incorporated in 5 to 10 g of xylene and tested in a varnish of the following composition:

| | |
|---|---|
| Synthacryl SC 303[1] (65%) | 27.51 g |
| Synthaccryl sc 370[1] (75%) | 23.34 g |
| Maprenal MF 650[2] (55%) | 27.29 g |
| butyl acetate/butanol (37/8) | 4.33 g |
| isobutanol | 4.87 g |
| Solvesso 150[3] | 2.72 g |
| white spirit K-30[4] | 8.74 g |
| Baysilon MA[5] (1% in Solvesso 150) | 1.20 g |
|  | 100.00 g |

[1]acrylate resin, ex Hoechst AG
[2]melamine resin, ex Hoechst AG
[3]ex ESSO
[4]ex Shell
[5]flow control agent, ex Bayer AG The varnish is diluted to a sprayable consistency with Solvesso 100 and sprayed on to a prepared aluminium sheet (coil coat, filler, silver metallic base paint) and stoved for 30 minutes at 130° C. to give a dry film thickness of 40–50 μm.

A varnish that contains no light stabiliser is used for comparison purposes.

The specimens are subjected to an accelerated weathering test (®UVCON, supplied by Atlas Corp.) as well as to an open-air weathering test.

The stabilised specimens have a better stability to weathering (gloss retention, no cracking) than the unstabilised comparison specimen.

What is claimed is:

1. A method of stabilizing an organic polymer against degradation caused by light, oxygen and heat, which comprises incorporating into said polymer an effective stabilizing amount of a compound of formula (1)

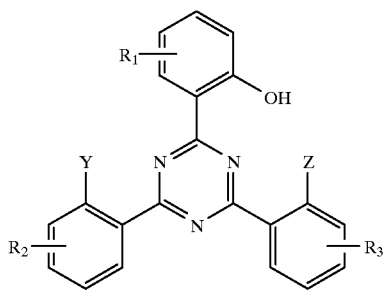

(1)

wherein $R_1$, $R_2$ and $R_3$ are each independently of one another hydrogen, halogen, $C_1$–$C_{18}$ alkyl or $C_1$–$C_{18}$ alkoxy;

one of Y and Z is hydrogen or $C_1$–$C_{18}$ alkoxy and the other is $C_1$–$C_{18}$ alkoxy;

with the proviso that, when $R_2$, $R_3$, Y and Z are each $C_1$–$C_{18}$ alkoxy, $R_1$ is not hydrogen; and with the proviso that at least one of $R_1$, $R_2$, $R_3$, Y and Z is not $C_1$–$C_{18}$ alkoxy.

2. A stabilized polymer according to claim 6, which is a binder for a surface-coating composition.

3. A stabilized polymer according to claim 2, which additionally contains one or more other stabilisers and/or modifiers.

4. A stabilised polymer according to claim 3, which additionally contains a light stabiliser selected from the group consisting of the sterically hindered amines, the 2-(2'-hydroxyphenyl)benzotriazoles and mixtures thereof.

5. A method according to claim 1 wherein the stabilized polymer is in a surface-coating composition.

6. A polymer stabilized, against degradation caused by light, oxygen and heat, by the method according to claim 1.

* * * * *